United States Patent
Baurmeister

(10) Patent No.: US 6,776,912 B2
(45) Date of Patent: Aug. 17, 2004

(54) HEMODIAFILTRATION SYSTEM AND METHOD

(75) Inventor: Ulrich Baurmeister, Wuppertal (DE)

(73) Assignee: Membrana GmbH, Wuppertal (DE)

( * ) Notice: Subject to any disclaimer, the term of this patent is extended or adjusted under 35 U.S.C. 154(b) by 103 days.

(21) Appl. No.: 10/168,502

(22) PCT Filed: Dec. 14, 2000

(86) PCT No.: PCT/EP00/12699

§ 371 (c)(1),
(2), (4) Date: Jun. 21, 2002

(87) PCT Pub. No.: WO01/47580

PCT Pub. Date: Jul. 5, 2001

(65) Prior Publication Data

US 2002/0190000 A1 Dec. 19, 2002

(30) Foreign Application Priority Data

Dec. 23, 1999 (DE) .......................... 199 62 287

(51) Int. Cl.[7] .................. B01D 61/00; B01D 63/02; A61M 1/34
(52) U.S. Cl. .............. 210/646; 210/321.79; 210/321.8; 210/321.81; 210/321.88; 210/321.89; 210/321.9; 210/433.1; 210/500.23; 210/650; 422/44; 604/4.01
(58) Field of Search .................... 210/321.79, 321.8, 210/321.81, 321.89, 321.9, 433.1, 500.23, 646, 650, 321.71, 321.88; 422/44, 48; 604/4.01, 5.04

(56) References Cited

U.S. PATENT DOCUMENTS

| | | |
|---|---|---|
| 4,861,485 A | 8/1989 | Fecondini |
| 5,660,722 A | 8/1997 | Nederlof |
| 5,725,949 A | 3/1998 | Pasquali et al. |
| 5,882,516 A | 3/1999 | Gross et al. |
| 5,919,370 A | 7/1999 | Röttger et al. |
| 6,635,179 B1 * | 10/2003 | Summerton et al. ........ 210/650 |

FOREIGN PATENT DOCUMENTS

| | | |
|---|---|---|
| DE | 28 51 929 A1 | 6/1980 |
| DE | 195 18 624 C1 | 11/1996 |
| DE | 196 07 162 C2 | 4/1998 |

(List continued on next page.)

OTHER PUBLICATIONS

B.L. Jaber et al., New Polyether Sulfone Dialyzers Attenuate Passage of Cytokine–Inducing Substances from *Pseudomonas aeruginosa* Contaminated Dialysate, Blood Purification, 1998, vol. 16, pp. 210–219.
U.S. patent application Ser. No. 10/089,943, Baurmeister, filed Apr. 5, 2002.

*Primary Examiner*—John Kim
(74) *Attorney, Agent, or Firm*—Oliff & Berridge, PLC

(57) ABSTRACT

A hemodiafiltration system for treating blood which has module having a housing in which hollow-fiber membranes are arranged in the direction of the longitudinal extent and are embedded at their ends in first and second sealing compounds joined to the inner wall of the housing in a fluid-tight manner. The membrane module also has a dialyzate space and a substituate space separated from the dialyzate space in a fluid-tight manner by a continuous dividing wall. The membrane module further includes means for delivering and withdrawing a dialyzate to and from the dialyzate space, and means for delivering a substituate to the substituate space. The hollow-fiber membranes are used for blood treatment, filtration of the substituate, and delivery of the substituate to the blood. An exterior space is formed around the hollow-fiber membranes that is delimited by the inner wall of the housing and sealing compounds and is divided along the longitudinal extent of the housing by a dividing wall into the substituate space and the dialyzate space, the dividing wall encloses each individual hollow-fiber membrane.

22 Claims, 5 Drawing Sheets

FOREIGN PATENT DOCUMENTS

| | | |
|---|---|---|
| EP | 0 079 781 A2 | 5/1983 |
| EP | 0 451 429 A2 | 10/1991 |
| EP | 0 692 269 A2 | 1/1996 |
| EP | 0 701 826 A2 | 3/1996 |
| EP | 0 732 141 A1 | 9/1996 |
| FR | 2 626 180 A1 | 7/1989 |
| JP | 10118472 | 5/1998 |

* cited by examiner

HEMODIAFILTRATION SYSTEM AND METHOD

BACKGROUND OF THE INVENTION

1. Field of the Invention

The invention relates to a hemodiafiltration system for treating blood, comprising a membrane module having a cylinder-shaped housing with a longitudinal extent, in which housing is included a bundle of hollow-fiber membranes having semipermeable walls capable of supporting fluid flow through their lumina. The ends of the hollow-fiber membranes are embedded in a manner in first and second sealing compounds joined to the housing inner wall in a fluid-tight manner and are arranged in the direction of the longitudinal extent. There is a dialyzate space into which a dialyzate inlet arrangement and a dialyzate outlet arrangement open, as well as a substituate space into which a substituate inlet arrangement opens, a means for delivering a dialyzate with a defined volume stream into the dialyzate space via the dialyzate inlet arrangement, a means for withdrawing the dialyzate from the dialyzate space via the dialyzate outlet arrangement, and a means for delivering a substituate with a defined volume stream into the substituate space via the substituate inlet arrangement. The membrane module is implemented as an integrated unit for blood treatment, filtration of the substituate, and mixing of the substituate with the blood. The substituate and dialyzate spaces are separated from each other in a fluid-tight manner via a continuous dividing wall. The invention furthermore relates to a membrane module for hemodiafiltration.

2. Discussion of Related Art

Hemodiafiltration is a combined membrane-based process for blood purification in which hemodialysis and hemofiltration are conducted concurrently. This process combines the advantages of convective substance transport in hemofiltration with those of diffusion in hemodialysis. In hemofiltration, blood is passed along one side of the membrane of a hemofilter and a portion of the blood liquid is withdrawn through the membrane by ultrafiltration. This partial stream is replaced by a sterile and pyrogen-free substitution liquid, or substituate, that is delivered to the extracorporeal blood stream either upstream from the hemofilter in the form of pre-dilution or downstream from the hemofilter in the form of post-dilution. In addition, in hemodiafiltration the usual hemodialysis is also conducted, wherein dialyzate is passed along the other side of the membrane of the hemodialyzer such that substances usually eliminated with the urine can be removed through the membrane.

The combination of diffusive substance transport with convective substance transport in hemodiafiltration permits the advantageous removal of more than only substances from the blood having a low molecular weight that are usually eliminated with the urine. Slowly diffusing medium-sized molecules with molecular weights from about 1 to 55 kD profit especially from the convective substance transport, and that is all the more so as these molecules increase in size and as the filtrate stream through the membrane increases. At about 60 kD, the membranes are intended to be essentially impermeable, so that the patient does not pass more than 4 g of protein from the blood into the dialyzate during a 4-hour treatment.

In the conventional hemodialysis process, only the amount of liquid the patient has taken in between the dialysis treatments is removed from the blood via the dialysis membrane as ultrafiltrate. The amount of liquid removed in this process is about 6 to 8% of the blood volume stream. In conducting current hemodialysis processes, so-called volume-controlled dialysis machines are generally used. They control the net amount of liquid removed according to the preset net filtration by balancing the dialyzate stream fed to the dialyzer with the dialyzate stream withdrawn from the dialyzer.

In hemodiafiltration, on the other hand, the amount of ultrafiltrate is significantly higher, from about 20 to 30% of the blood volume stream, due to the liquid fraction needed to increase the convective transport through the membrane. In the end, the net amount of liquid withdrawn from the patient is the same as that in conventional hemodialysis. The amount of liquid exceeding that needed to increase the convective transport is, as noted, replaced by a substituate.

To conduct hemodiafiltration processes, modified dialysis machines are generally used that permit control of the ultrafiltration rates and balance the ultrafiltration and substituate volume streams.

Different requirements are usually imposed with respect to the purity of the dialyzate and substitution liquids. The dialyzate can be prepared online from fresh water and an electrolyte concentrate, where the fresh water is normally germ-free and the electrolyte concentrate inherently sterile. The substitution liquid itself can be prepared online from the dialyzate, but it is not generally required that the dialyzate prepared online is absolutely sterile and free of endotoxins, pyrogens and CIS.

Endotoxins are cell remnants of dead bacteria. The endotoxin concentration is usually determined using the so-called LAL test, a biological assay such as that manufactured by BioWhittaker, Inc., for example. Pyrogens are temperature-elevating substances. When infused in rabbits, for example, they cause an increase in body temperature. Pyrogens can include endotoxins and exotoxins. The latter are produced by living bacteria. In human blood, these substances lead to stimulation of monocytes that themselves produce cytokines and thus trigger a cascade of additional cell stimulations. Today, endotoxins, exotoxins, pyrogens, and other substances from the dialyzate that stimulate the blood are grouped under the abbreviation CIS (cytokine inducing substances). One of the relevant cytokines produced by stimulation of stimulated monocytes is interleukin 6 (IL 6). The determination of CIS by detection of IL 6 is described in B. L. Jaber et al., Blood Purif. 1998, Vol. 16, pp. 210–219, for example.

For this reason, the dialyzate for preparing the substitution liquid should be converted to the sterile and ideally CIS-free state, using a filter, for example. Of course, the substitution liquid prepared in this manner can also be used itself as dialyzate. Modem dialysis machines generally include a facility with which the dialyzate is filtered online such that it has an endotoxin concentration of less than 0.5 EU per ml of dialyzate. As a result, patients experience almost no pyrogen reactions, even in the case of so-called high-flux dialysis, which are frequently observed with dialyzate contaminated with endotoxins. However, with an endotoxin concentration of <0.03 EU/ml, which is the detection limit of the conventional LAL tests, CIS might still be present in the dialyzate. The requirement for CIS-free dialyzate is therefore more stringent than that for LAL-negative dialyzate.

In EP-A 692 269, a hemodiafiltration apparatus is described with two blood filters connected in series. The blood filters each contain membranes, one side of which is subjected to a flow of blood to be purified and the other side to dialyzate flow. The dialyzate fed to the hemodiafiltration apparatus was previously passed through a sterile filter. In the apparatus described in EP-A 692 269, a transfer of dialyzate as a substitution liquid directly into the blood takes place in one of the two blood filters in the direction of the blood flow, due to the positive transmembrane pressure set at this point via the membrane of this blood filter. A negative transmembrane pressure is generated in the second blood filter, where separation of a portion of the blood liquid and removal into the dialyzate of substances normally eliminated with the urine take place via diafiltration.

Such hemodiafiltration apparatus with blood filters connected in series are complex in operation and can generally not be used in commercially available dialysis machines due to the design and the special and complex controls associated with it.

EP-A 451 429 also discloses a hemodiafiltration apparatus having two membrane modules connected in series. In this case, the first membrane module is a hemofilter in which a partial stream of liquid is withdrawn by ultrafiltration from the blood to be purified, wherein the partial stream primarily contains the medium-molecular substances to be removed from the blood. The ultrafiltrate is regenerated in a special filter and reintroduced to the blood stream before the latter is directed into the second membrane module. This blood stream is then subjected to hemodialysis in the second membrane module.

In addition to the previously cited disadvantages of separate blood filters connected in series, the hemodiafiltration apparatus described in EP-A 451 429 has the drawback that it requires a special regenerator that must be used to purify the ultrafiltrate.

In DE-A 196 07 162, a hemodiafiltration system is described with controlled delivery of a substituate and a dialyzate into a dialyzer, wherein the dialyzer is designed as a single component for blood treatment, substituate filtering, and mixing of the substituate with the blood to be treated. The dialyzer contains two adjacent membrane modules in its longitudinally extended housing, each with a bundle of hollow-fiber membranes. The membrane modules are separated from each other by a dividing wall substantially parallel to the hollow-fiber membranes. The first membrane module is used for hemodiafiltration and the second membrane module for sterile filtration of the substituate. The dialyzer further comprises a chamber in which purified substituate is reunited with the blood to be treated.

While the hemodiafiltration system described in DE-A 196 07 162 has a simpler and clearer construction compared to the systems with multiple blood filters connected in series, the manufacture of the two-module dialyzers disclosed in DE-A 196 07 162 is difficult, particularly due in part to the handling of two different hollow-fiber membrane bundles. Furthermore, the membrane modules in the dialyzer are not arranged rotationally symmetrically, so that there is a risk of non-uniform flow, in particular through the external space surrounding the hollow-fiber membranes of the first membrane module, which is used for hemodiafiltration.

SUMMARY OF THE INVENTION

It is therefore an object of the present invention to provide a hemodiafiltration system that has a simple construction, allows a predeterminable and reproducible delivery of substituate and dialyzate, and can be used in volume-controlled dialysis machines without major modifications. It is a further object of the present invention to provide a membrane module for hemodiafiltration for use in a hemodiafiltration system, wherein the module enables concurrent sterile filtration of the substituate.

The object is, on the one hand, achieved by a hemodiafiltration system wherein the hollow-fiber membranes are combined into a single bundle and the hollow-fiber membranes are used for blood treatment, filtration of the substituate, and delivery of the substituate to the blood. An exterior space delimited by the housing inner wall and the first and second sealing compounds is formed around the hollow-fiber membranes, wherein the exterior space along the longitudinal extent of the housing is separated by a dividing wall into the substituate space and the dialyzate space. The dividing wall enclosing each individual hollow-fiber membrane.

In a preferred embodiment of the hemodiafiltration system of the invention, the housing of the membrane module used according to the invention is circularly cylindrical about its longitudinal axis oriented in the direction of the longitudinal extent, and the hollow-fiber membranes are arranged in a bundle that is substantially rotationally symmetrical about the longitudinal axis.

DESCRIPTION OF PREFERRED EMBODIMENTS

Figure 1:
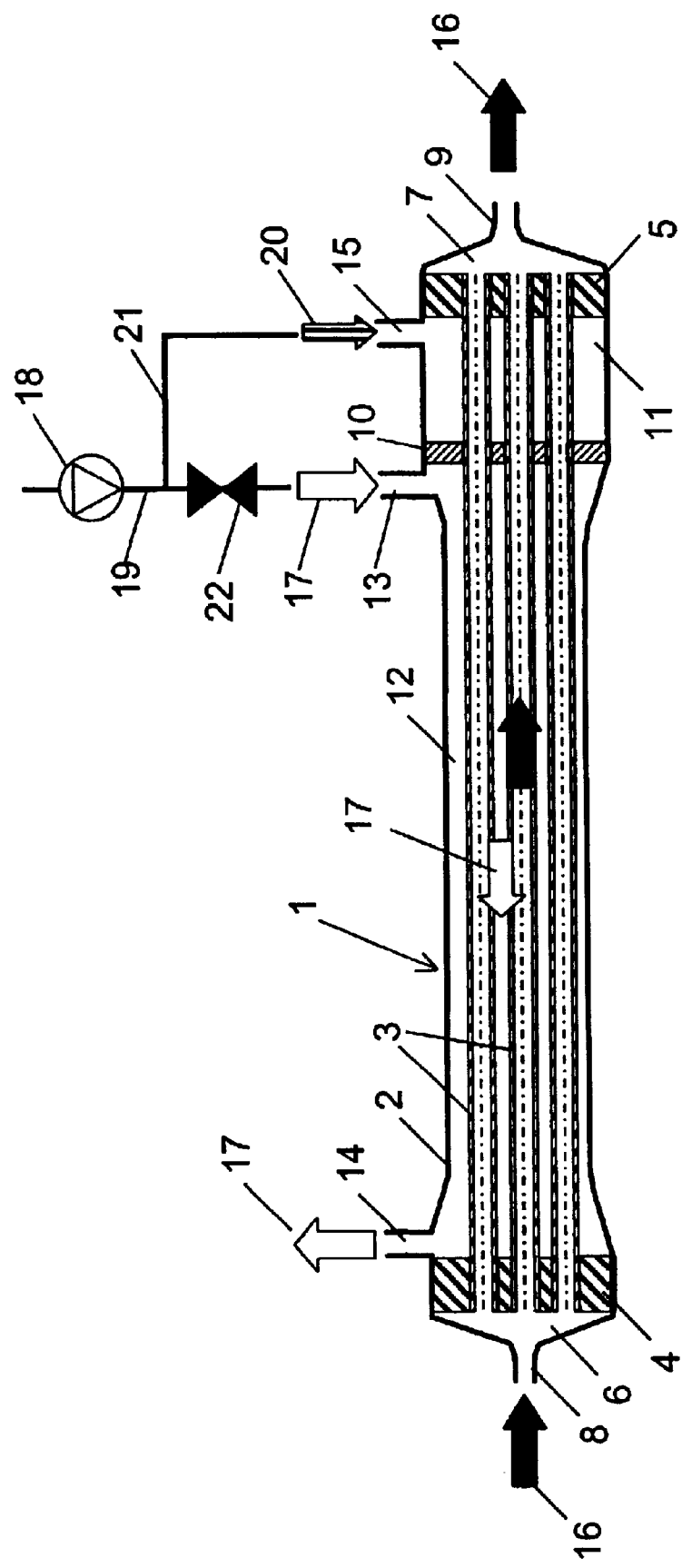
FIG. 1 represents a segment of a hemodiafiltration system of the invention, with a membrane module employed therein, in longitudinal section illustrating a process with post-dilution of the blood.

In the membrane module of the hemodiafiltration system of the invention, the ends of the hollow-fiber membranes are each embedded in a fluid-tight manner in sealing compounds that also seal off the exterior space formed around the hollow fibers with respect to a distribution space, in which the blood to be treated and introduced into the distribution space via a blood inlet arrangement is distributed to the lumina of the hollow-fiber membranes, and with respect to a collection space in which the blood flowing from the lumina is collected and withdrawn from the module via a blood outlet arrangement. The ends, open on the face, of the hollow-fiber membranes extend through the respective sealing compound and are in communication with the distribution and collection spaces via the lumina, so that the blood to be treated can pass through the membranes.

Due to the fact that in the membrane module used in the hemodiafiltration system of the invention, the same hollow-fiber membranes are used for blood treatment, filtering of the substituate, and delivery of the substituate to the blood, and that the dialyzate and substituate spaces are separated from each other by a dividing wall, the dialyzate and substituate spaces are arranged adjacent to each other at different positions along the hollow-fiber membranes when viewed in the direction of the extent of the hollow-fiber membranes, with the dividing wall filling out the inner cross-section of the housing. Preferably, the dividing wall in the membrane module used in the hemodiafiltration system of the invention is arranged substantially transversely to the hollow-fiber membranes.

During use of the hemodiafiltration system according to the invention, the blood to be purified, which is withdrawn from the patient, is directed into the membrane module via the blood inlet arrangement and through the lumina of the hollow-fiber membranes. By a means for delivery of dialyzate, which comprises suitable delivery means, e.g., in the form of a pump or metering unit for delivering dialyzate with a defined volume stream, and a dialyzate supply line connected to the dialyzate inlet arrangement, fresh dialyzate with a defined volume stream is supplied to the membrane module and introduced into the dialyzate space via the dialyzate inlet arrangement. In the dialyzate space, the dialyzate is passed along the hollow-fiber membranes, thereby also taking up the ultrafiltrate withdrawn from the blood through the walls of the hollow-fiber membranes via ultrafiltration. Hemodiafiltration of the blood takes place in the dialyzate space area, wherein substances normally eliminated with the urine are removed from the blood via diffusive and convective transport mechanisms. The dialyzate, mixed with the ultrafiltrate, is withdrawn from the dialyzate space via the dialyzate outlet arrangement using a dialyzate flow pump and conducted away via a dialyzate withdrawal line.

The substituate is introduced, via dedicated means for delivery of substituate with a defined volume stream, under increased pressure into the substituate space via the substituate inlet arrangement and delivered at that point with a defined volume stream to the blood flowing through the lumina of the hollow-fiber membranes, via the walls of the segments of the hollow-fiber membranes located in the substituate space. The amount of substituate to be delivered per unit of time, i.e., the substituate volume stream, is the difference between the liquid stream withdrawn from the blood in the dialyzate space area via ultrafiltration and the net filtration controlled and fixedly preset by the dialysis machine. In this process, the substituate volume stream is generally smaller than the dialyzate stream introduced into the dialyzate space. Depending on the direction of blood flow through the hollow-fiber membranes, the substituate can be delivered to the blood before the blood is subjected to hemodiafiltration (pre-dilution) or after it has been subjected to hemodiafiltration (post-dilution). Control of the dialyzate circuit, including substituate delivery, is performed by a balancing unit connected to the dialyzate circuit. The net filtration, i.e., the net amount of liquid to be withdrawn from the blood in the dialyzate space area, is adjusted by an ultrafiltrate pump coupled to the balancing unit using closed-loop control techniques.

In an embodiment of the hemodiafiltration system of the invention, the substituate delivery means is physically and completely separate from the dialyzate delivery means and comprises suitable delivery means for delivering the substituate with a defined volume stream, for example, in the form of a pump or a metering unit, and, separate from the dialyzate supply line, a substituate supply line in fluid communication with the substituate inlet arrangement. In this case, the dialyzate delivery means and substituate delivery means must be controlled separately by closed-loop control systems coupled to one another.

In a preferred embodiment of the hemodiafiltration system of the invention, the substituate delivery means and dialyzate delivery means are coupled to one another. It is especially preferred for the coupling to be implemented such that the substituate delivery means and the dialyzate delivery means comprise a common multiple pump to which a dialyzate supply line in communication with the dialyzate inlet arrangement and a substituate supply line in communication with the substituate inlet arrangement are connected. This multiple pump comprises a common pump drive to which two separate pump heads are coupled. The ratio of the substituate volume stream to that of the dialyzate can be adjusted via the delivery rate of the pump heads.

In another especially preferred embodiment, the dialyzate delivery means comprises a dialyzate delivery device and dialyzate supply line, and the substituate delivery means comprises a substituate supply line, and the substituate supply line branches off from the dialyzate supply line via a diversion. In this case, the substituate is withdrawn from the dialyzate supply line by the diversion as a partial stream from the dialyzate flowing through the dialyzate supply line and directed via the substituate supply line and substituate inlet arrangement into the substituate space, from which it is delivered to the blood flowing through the hollow-fiber membranes via their walls.

To establish a defined substituate stream, it is especially preferable for a pump to be inserted in the substituate supply line, wherein the pump provides a defined delivery of the substituate, i.e., allows adjustment of the substituate volume stream. It is preferred in this case for the pump to be controllable. The adjustment of the dialyzate and substituate volume streams, and the ratio of these volume streams to each other, can also be performed by throttles. For this reason, in a likewise especially preferred embodiment, a throttle is inserted in the dialyzate supply line in the area between the diversion and dialyzate inlet arrangement or into the substituate and dialyzate supply lines in the area between the diversion and dialyzate inlet arrangement, the throttle providing a means for adjusting the ratio of substituate volume stream to dialyzate volume stream.

A throttle in this case is understood to be a defined restriction of a flow cross-section to selectively generate a defined pressure drop when a fluid flows through this restriction. That is, the throttle exhibits a reduced flow cross-section compared to the flow cross-section before and after the throttle with respect to the direction of flow. In this embodiment, the flow cross-section of the throttle has a defined fixed value independent of the passing medium, or it can be adjusted to a defined value independent of the passing medium. In such throttles, the pressure drop arising during flow can be predetermined. Throttles with a fixed flow cross-section are, for example, perforated or slit diaphragms having a flow cross-section preferably adjustable to the fixed cross-section, or capillary tubes with defined diameters. Throttles with adjustable cross-section are, for example, valves or throttle flaps inserted into piping. It is preferred for the throttles of the invention to be adjustable, and it is especially preferred for the throttles to be controllable.

The dialyzate stream is introduced into the dialyzate space by the throttles arranged in the dialyzate and/or substituate supply lines and the substituate stream, and thereby the ratio of the two streams to one another can be adjusted to a defined value in a simple manner.

The hemodiafiltration system of the invention is considerably simpler compared to prior art systems due to the membrane module employed according to the invention, in which, during use, the dilution of the blood with substituate, as required for hemodiafiltration, and the hemodiafiltration are integrated in a single membrane module in a simple, controllable, and reproducible manner, and which, like conventional hemodialyzers, contains a single bundle of hollow-fiber membranes. At the same time, the concept of the invention of separately delivering dialyzate and substituate via respective means into the dialyzate and substituate spaces, which are separated from each other in a fluid-tight manner, permits selective adjustment of the required dialyzate and substituate volume streams to adapt to the hemodiafiltration application. Furthermore, using the hemodiafiltration system of the invention, hemodiafiltration can be conducted in commercially available dialysis machines with volume-stream controlled ultrafiltration.

DE-A 28 51 929 discloses a module design on the basis of hollow-fiber membranes, herein the dialyzate space is divided into two sections by an impermeable dividing wall. In one embodiment, dialyzate is directed through the one section, which is provided with an inlet arrangement and an outlet arrangement in order to remove, by diffusion, substances normally eliminated with the urine from the blood flowing through the hollow-fiber membranes. The second section, which is provided with an outlet arrangement, is subjected to a partial vacuum in order to extract, via the walls of the hollow-fiber membranes, a filtrate from the blood flowing through the membranes. DE-A 28 51 929, however, does not disclose the inclusion of such a membrane module in a hemodiafiltration system or the use of such a membrane module in a hemodiafiltration process.

Therefore, a further subject of the invention is the use of a membrane module having a cylinder-shaped housing with a longitudinal extent, in which housing a bundle of hollow-fiber membranes having semipermeable walls, capable of supporting fluid flow through their lumina, and embedded at their ends in first and second sealing compounds joined to the housing inner wall in a fluid-tight manner is arranged in the direction of the longitudinal extent, and in which housing an exterior space delimited by the housing inner wall and the first and second sealing compounds is formed around the hollow-fiber membranes. The exterior space along the longitudinal extent of the housing is divided by a continuous dividing wall into a dialyzate space and a substituate space separated from the dialyzate space in a fluid-tight manner. The dividing wall encloses each individual hollow-fiber membrane, to conduct a hemodiafiltration process in which the bundle of hollow-fiber membranes is used, in addition to the actual blood treatment, to filter the substituate and deliver the substituate to the blood.

In the membrane module of the hemodiafiltration system according to the invention, the delivery of the substituate to the blood can take place before or after the blood is subjected to hemodiafiltration in the dialyzate space area. In an individual case, it is also possible to divide the substituate space, and thus the delivery of the substituate to the blood, along the extent of the hollow-fiber membranes and deliver one part of the substituate to the blood before and one part after the hemodiafiltration. In this case, in the membrane module of the invention, for example, two substituate-space sections are arranged along the extent of the hollow-fiber membranes adjacent to the embedding point of the hollow-fiber membrane ends, each section is separated by a dividing wall from an intermediate dialyzate space in a fluid-tight manner. Correspondingly, it is also possible to divide the dialyzate space, and thereby the hemodiafiltration, and to arrange two dialyzate-space sections in the membrane module, for example, along the extent of the hollow-fiber membranes adjacent to the embedding points of the hollow-fiber membrane ends. Each section is separated by a dividing wall from an intermediate substituate space.

For applications in which a post-dilution of the blood with substituate takes place, the blood flows into the hollow-fiber membranes at the end of the membrane module facing the dialyzate space and through the membranes toward the end facing the substituate space. The required liquid is first withdrawn from the blood in the dialyzate space area by ultrafiltration and then substituate delivered to the blood in the substituate space area. In this process, it is advantageous if the dialyzate inlet arrangement is adjacent to the dividing wall and the dialyzate outlet arrangement adjacent to the sealing compound delimiting the dialyzate space and enclosing the ends of the hollow-fiber membranes. The dialyzate then flows through the dialyzate space in a direction opposite that of the blood flow.

For applications in which a pre-dilution of the blood with substituate takes place, the blood flows into the hollow-fiber membranes at the end of the membrane module facing the substituate space and through the membranes toward the end facing the dialyzate space. In this process, substituate is first delivered to the blood in the substituate space area and then the required liquid withdrawn by ultrafiltration in the dialyzate space area. In this case, it is advantageous if the dialyzate inlet arrangement is adjacent to the sealing compound delimiting the dialyzate space and enclosing the ends of the hollow-fiber membranes, and the dialyzate outlet arrangement is adjacent to the dividing wall so that the dialyzate flows through the dialyzate space in a direction opposite that of the blood flow.

In conducting hemodiafiltration, an external sterile filter is often connected upstream from the actual membrane module, providing sterile filtration of the dialyzate or at least the liquid delivered as a substituate. Generally, however, a sterile filtration of the entire dialyzate is unnecessary, since in the end the portion of the dialyzate passed as dialyzate along the hollow-fiber membranes is not subject to the stringent purity requirements applying to the substituate. For the sterile filtration of the substituate, in an advantageous embodiment of the hemodiafiltration system according to the invention, a sterile filter is arranged within the membrane module around the hollow-fiber bundle in the substituate space area, the filter enclosing the hollow-fiber membrane bundle.

The invention further relates to a membrane module comprising a cylinder-shaped housing with a longitudinal extent, in which housing a bundle of hollow-fiber membranes with semipermeable walls and capable of supporting fluid flow through their lumina is arranged in the direction of the longitudinal extent of the housing, the ends of the hollow-fiber membranes being embedded in a fluid-tight manner in first and second sealing compounds joined to the housing inner wall in a fluid-tight manner such that an exterior space delimited by the first and second sealing compounds and the housing inner wall is formed around the hollow-fiber membranes. The exterior space along the longitudinal extent of the housing is divided into a dialyzate space and a substituate space by a dividing wall that encloses each hollow-fiber membrane and is arranged substantially transversely to the hollow-fiber membranes. The dialyzate space has an inlet arrangement and an outlet arrangement for introducing and withdrawing a dialyzate and the substituate space has at least one opening for introducing a substituate, wherein a sterile filter is arranged in the substituate space area between the substituate inlet arrangement and the hollow-fiber membranes located in the substituate space. The sterile filter divides the substituate space into an outer substituate-space section and an inner substituate-space section that is spatially separated from the outer substituate-space section by the sterile filter. The outer substituate-space section is in fluid communication with the substituate inlet arrangement and the hollow-fiber membranes is arranged in the inner substituate-space section.

Spatial separation in this case is understood to be the state in which a fluid introduced into the outer substituate-space section by the substituate inlet arrangement can enter the inner substituate-space section only by the sterile filter itself, i.e., the sterile filter acts as a so-called dead-end filter.

In a preferred embodiment of the membrane module of the invention, the sterile filter is arranged around and encloses the hollow-fiber membrane bundle. In this preferred embodiment, the sterile filter divides the substituate space perpendicularly to the hollow-fiber membranes into the outer substituate-space section, wherein a uniform distribution of the substituate to the sterile filter can take place, and the inner substituate-space section contains the bundle of hollow-fiber membranes. A possibly pleated flat membrane can be used advantageously as a sterile filter. It is advantageous to use a flat membrane that is consistently microporous. The sterile filter is preferably impermeable to endotoxins and especially preferably impermeable to CIS, thereby ensuring during use the delivery of a sterile substituate to the hollow-fiber membranes that is free of endotoxins and pyrogens and preferably of CIS. In this case, a sterile filter impermeable to endotoxins is understood to be one for which, in filtering a contaminated dialyzate with an endotoxin concentration of up to 30 EU/ml at a filtration rate of 150 ml/min over 4 hours through the sterile filter, the filtrate has an endotoxin concentration below the detection limit of conventional tests, i.e., below about 0.03 EU/ml. The endotoxin concentration in this case is determined using conventional LAL tests such as those sold and described by BioWhittaker, Inc. (MULTI-TEST LIMULUS AMEBOCYTE LYSATE PYROGENT®).

In individual cases, when employing the membrane module of the invention or used in the hemodiafiltration system according to the invention, it is also possible to embed additional semipermeable membrane elements in the sealing compound adjacent to the substituate space in which the hollow-fiber membrane ends are embedded in order to increase the substituate stream to be delivered to the blood. The flow through these membrane elements is then performed in dead-end mode, and they provide fluid communication between the substituate space and the space on the other side of the sealing compound, wherein this space is the distribution or collection space for the blood depending on the embodiment of the membrane module of the invention. A portion of the substituate can likewise be delivered via these membrane elements to the blood then located in the adjacent collection or distribution space. These semipermeable membrane elements can be present, for example, in the form of capillary membranes that are closed at one end, are preferably consistently microporous, are embedded in the sealing compound, and extend into the substituate space at their closed end. These membrane elements are, like the aforementioned sterile filter, preferably impermeable to endotoxins and especially preferably to CIS. Concerning the definition of endotoxin and CIS impermeability and the respective measurement methods, refer to the preceding discussion.

For use, it is advantageous for the dividing wall of the membrane module of the invention or used in the hemodiafiltration system according to the invention to be made of a substantially dimensionally stable material, i.e., a material that in use substantially retains its dimensions under the then prevailing conditions and in particular does not swell in the presence of the liquids used in this case, i.e., primarily the dialyzate. To simplify manufacture, the dividing wall is preferably composed of a cured sealing compound in which the hollow-fiber membranes are embedded such that the dividing wall encloses each hollow-fiber membrane. It is especially preferable for the dividing wall and first and second sealing compounds to be made of the same material. In this case, the materials commonly used as sealing compounds for embedding hollow-fiber membranes, such as cured polyurethane resins, epoxy resins, and the like can be used.

In the use of the hemodiafiltration system or membrane module of the invention, a maximally uniform distribution of substituate and dialyzate over the bundle cross-section is necessary in the membrane module. A uniform distribution can be achieved by an appropriate housing design. Preferably, the housing of the membrane module is designed such that it tightly encloses, with its inside, the bundle of hollow-fiber membranes in the predominant portion of the dialyzate space and exhibits an expansion of its cross-section in the area of the sealing compounds, dividing wall, and substituate space. In an advantageous embodiment, ring-shaped spaces are thereby formed around the bundle of hollow-fiber membranes in these areas in order to distribute the dialyzate over the hollow-fiber membrane bundle, collect the dialyzate from the membrane bundle, and/or distribute the substituate over the bundle.

Preferably, the bundle has, at least in the predominant portion of the dialyzate space, a packing density of the hollow-fiber membranes between 40 and 65%, in reference to the bundle cross-sectional area and substantially uniform in this area over the extent of the bundle. It has been observed that, for the membrane module of the invention or used according to the invention, such packing densities allow good removal from the blood of the substances normally eliminated with the urine.

In a likewise advantageous embodiment, the housing of the membrane module is designed such that it tightly encloses, with its inside, the bundle of hollow-fiber membranes in the dialyzate space area and exhibits an expansion of the housing cross-section in the area of the sealing compounds, dividing wall, and substituate space, and the hollow-fiber membrane bundle is arranged in the housing such that the cross-section of the hollow-fiber membrane bundle expands in the area of the dividing wall and substituate space. The packing density of the hollow-fiber membranes in this area is thereby less than in the predominant portion of the dialyzate space. It is especially preferred for the packing density of the hollow-fiber membrane bundle to be substantially homogeneous over the cross-section in the area of the expanded cross-section. As a result, the hollow-fiber membranes in the interior of the bundle are also easily accessible to the dialyzate or substituate, and the substituate flows uniformly into all hollow-fiber membranes of the bundle. The manufacture of the membrane module is also simplified through this embodiment since in the case of a dividing wall having a sealing compound, the sealing compound can better enclose the individual hollow-fiber membranes when they are embedded. In its expanded portion, the bundle preferably has a packing density between 20 and 55%, in reference to the respective bundle cross-sectional area.

To conduct an efficient hemodiafiltration, it is necessary that a sufficiently large exchange surface area be available for diafiltration in order to efficiently remove the substances normally eliminated with the urine from the blood. On the other hand, a sufficient membrane surface area must also be available in order to permit reliable delivery of the required amount of substituate to the blood. It is found for the membrane module of the present invention that, when viewed in the direction of the extent of the hollow-fiber membranes, the ratio $L_d/L_s$ of the length $L_d$ of the dialyzate space to the length $L_s$ of the substituate space should preferably be greater than 3. For this reason, the ratio $L_d/L_s$ is preferably between 3 and 20 and especially preferably between 5 and 15.

To likewise provide as large a membrane surface area as possible for substituate delivery to the blood and for hemodiafiltration, the dividing wall of the membrane module should be as thin as possible. On the other hand, a certain minimum thickness is necessary to ensure sufficient stability of the dividing wall. It is therefore advantageous for the dividing wall to have a thickness between 1 and 15 mm and especially advantageous to have a thickness between 5 and 10 mm.

For efficient hemodiafiltration, it is necessary to generate a sufficiently high convective transport in order to remove in particular the slowly-diffusing substances normally eliminated with the urine, having medium molecular weight. Moreover, it is advantageous if only a relatively small section of the hollow-fiber membrane bundle is needed for the delivery of substituate to the blood. This means that a sufficiently high filtrate flow through the membrane wall must be realizable. For this reason, the hollow-fiber membranes present in the membrane module of the invention or used according to the invention have an ultrafiltration rate for water between 20 and 1500 mL/(h·m²·mmHg). The ultrafiltration rate in this case is determined using the method described in DE-A 195 18 624, and express reference is hereby made to its disclosure in this regard.

For the reliable operation of the hemodiafiltration system of the invention, it is important that no undesired contamination of the blood flowing through the hollow-fiber membranes with bacteria, endotoxins, or pyrogens occurs, in particular when delivering the substituate to the blood. As previously discussed, the dialyzate and/or at least the substituate can, to this end, be subjected to a sterile filtration in a separate sterile filter or one integrated in the membrane module of the hemodiafiltration system according to the invention. Alternatively or in addition, this sterile filtration can also take place in the hollow-fiber membranes themselves of the membrane module of the hemodiafiltration system of the invention. Therefore, in a preferred embodiment the hollow-fiber membranes are impermeable to endotoxins and especially preferably impermeable to cytokine-inducing substances. The impermeability in this case can be achieved by an appropriately adjusted pore size of the functional separation layer of the membranes and/or by adsorptive properties of the hollow-fiber membranes. Concerning the definition of endotoxin and CIS impermeability and the respective measurement methods, refer to the preceding discussion.

The hollow-fiber membranes used according to the invention preferably have an inside diameter between 140 and 260 pm, with a wall thickness preferably between 5 and 100 $\mu$m and more preferably between 20 and 60 $\mu$m. Membrane materials are preferably those having good blood compatibility. This includes polymers from the group of cellulosic polymers such as cellulose or regenerated cellulose, modified cellulose such as cellulose esters, cellulose ethers, amine-modified celluloses, and mixtures of cellulosic polymers, from the group of synthetic polymers such as polyacrylonitrile and corresponding copolymers, polyarylsulfones, and polyarylethersulfones such as polysulfone or polyethersulfone, polyamides, polyether block amides, polycarbonates, or polyesters, as well as modifications, blends, mixtures, or copolymers derived from these polymers. These polymers or polymer mixtures can contain additional polymers such as polyethylene oxide, polyhydroxyether, polyethylene glycol, polyvinylpyrrolidone, polyvinyl alcohol, or polycaprolactone as additives. In individual cases, the membrane can, for example, also have been subjected to a surface modification in order to give certain properties to the membrane surface, for example, in the form of certain functional groups, or to achieve the hydrophilation of an otherwise hydrophobic membrane on its surfaces, as is described for example in JP-A 101 18472.

No restrictions are placed on the construction of the bundle of hollow-fiber membranes arranged in the membrane module of the hemodiafiltration system of the invention, i.e., the arrangement of the hollow-fiber membranes in the bundle. A good flow around the individual hollow-fiber membranes should be ensured, however. In an advantageous construction, the hollow-fiber membranes are substantially parallel to each other and to the longitudinal axis of the bundle and the spacing between them is maintained by textile threads. This can be achieved, for example, before the bundle is assembled, by using the textile threads to weave the hollow-fiber membranes to form a mat or ribbon of parallel hollow-fiber membranes and then configuring them to form a bundle. The bundle of hollow-fiber membranes contained in the membrane module of the invention can also be composed of bundle sections, as long as during use each of the hollow-fiber membranes of the bundle contributes to blood treatment, filtration of the substituate, and delivery of the substituate to the blood. Such a construction of bundle sections, in which the sections are wrapped with threads to improve the flow around the hollow-fiber membranes and the hollow-fiber membranes within the sections are spaced using support threads, is described in EP-A 732 141, for example. Moreover, the hollow-fiber membranes can also exhibit an undulation.

FIG. 1 is a schematic representation of a segment of a hemodiafiltration system according to the invention with membrane module 1 in longitudinal section. The membrane module 1 has a cylinder-shaped housing 2 in which a bundle of hollow-fiber membranes 3 is arranged, wherein the membranes are oriented in the direction of the longitudinal extent of the housing. The ends of the hollow-fiber membranes are embedded in a fluid-tight manner in sealing compounds 4, 5, which are themselves joined to the inner wall of housing 2 in a fluid-tight manner. The hollow-fiber membranes are embedded in sealing compounds 4, 5 such that their ends extend through the sealing compounds 4, 5 and their lumina open into a distribution space 6 and a collection space 7. The distribution space 6 has a blood inlet arrangement 8 and the collection space 7 has a blood outlet arrangement 9.

Encircling the hollow-fiber membranes 3 between sealing compounds 4, 5 and the inner wall of housing 2 is an exterior space that is divided into a substituate space 11 and a dialyzate space 12 along the extent of the hollow-fiber membranes 3 by a dividing wall 10 running transversely to the hollow-fiber membranes 3 and made for example of a cured epoxy or polyurethane sealing compound. The dividing wall 10 encloses the individual hollow-fiber membranes 3 and is joined in a fluid-tight manner to the housing inner wall, so that the substituate space 11 and dialyzate space 12 are separated from each other in a fluid-tight manner.

The dialyzate space has a dialyzate inlet arrangement 13 and dialyzate outlet arrangement 14, and the substituate space has a substituate inlet arrangement 15. To ensure a good distribution of dialyzate and substituate in the dialyzate space 12 and substituate space 11, respectively, during use, housing 2 in the membrane module illustrated in FIG. 1 has an expanded cross-section in the area of dividing wall 10 and substituate space 11. In the area of outlet arrangement 14, the cross-section of housing 2 is also expanded in order to allow uniform withdrawal of the dialyzate from the module.

FIG. 1 schematically indicates a process for hemodiafiltration in which a post-dilution of the blood with substituate takes place, i.e., the ultrafiltrate is first removed from the blood as it flows through the membrane module and the substituate is then delivered to the blood. During use, the blood, indicated by arrows 16, flows via the blood inlet arrangement 8 into the distribution space 6, through the lumina of the hollow-fiber membranes 3, then out of the hollow-fiber membranes 3 into the collection space 7, and is conducted out of the membrane module, i.e., out of the hemodiafilter, via the blood outlet arrangement 9.

The dialyzate, indicated by arrows 17, is introduced into the dialyzate space 12 via dialyzate supply line 19 connected to inlet arrangement 13 using a pump 18, which serves as a delivery device, and flows through the dialyzate space 12 in a direction opposite to that of the blood flow. In this process, the dialyzate 17 takes up the ultrafiltrate flowing out through the walls of the hollow-fiber membranes 3, together with the substances removed from the blood that are normally eliminated with the urine. The dialyzate 17, mixed with the ultrafiltrate, is withdrawn from the dialyzate space 12 via the outlet arrangement 14.

In the embodiment illustrated in FIG. 1, the substituate represented by arrow 20 is withdrawn from the dialyzate flowing through dialyzate supply line 19 as a partial stream via a substituate supply line 21 branching off from the dialyzate supply line 19 and introduced into the substituate space 11 via the inlet arrangement 15, where it flows through the hollow-fiber membranes extending through at this location and mixes with the blood flowing through the hollow-fiber membranes 3. To establish a defined ratio of dialyzate volume stream to substituate volume stream, a throttle 22 is inserted in the dialyzate supply line 19 in the area between the diversion and the dialyzate inlet arrangement 13.

Figure 2:
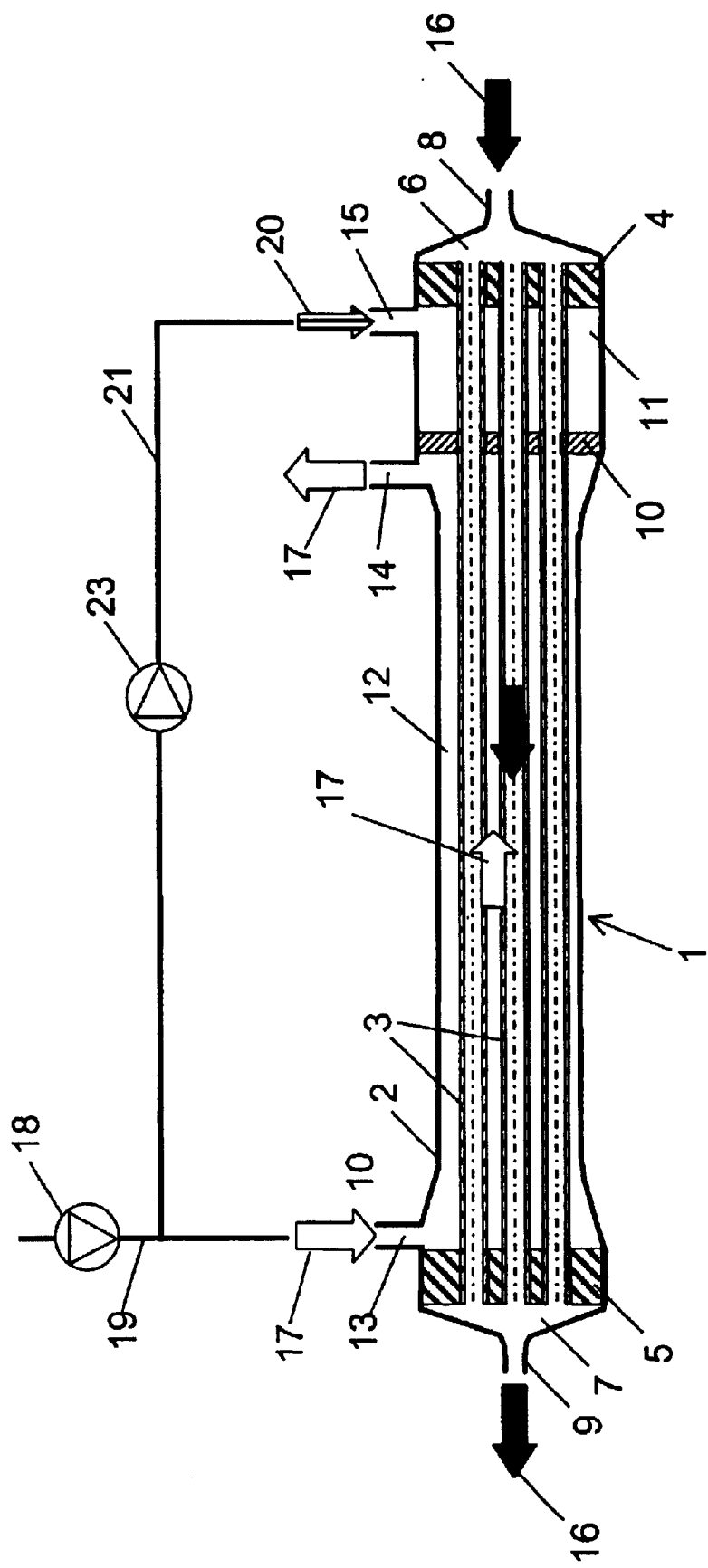
FIG. 2 represents a segment of a hemodiafiltration system of the invention, with a membrane module employed therein, in longitudinal section illustrating a process with pre-dilution of the blood.

The membrane module represented schematically in longitudinal section in FIG. 2 corresponds to a substantial extent to that in FIG. 1, so that the same components are designated with the same reference numbers and a detailed description is not repeated. FIG. 2, however, shows a segment of a hemodiafiltration system in which, during use, a pre-dilution of the blood takes place during hemodiafiltration, i.e., substituate is initially delivered to the blood as it flows through the membrane module and the ultrafiltrate is then withdrawn.

During hemodiafiltration, the blood 16 is directed via blood inlet arrangement 8 and distribution space 6 into, and flows through, the hollow-fiber membranes 3. In this process, substituate is delivered to the blood in the area of substituate space 11 and the blood thereby diluted with substituate before it passes, on its way through the hollow-fiber membranes 3, through the area of dialyzate space 12, in which the required liquid is withdrawn from the blood by ultrafiltration through the walls of the hollow-fiber membranes and the substances normally eliminated with the urine are removed thereby. The purified blood, adjusted to the required liquid content, leaves the membrane module of the invention via the blood outlet arrangement 9.

The dialyzate 17 is introduced via the inlet arrangement 13, which in this case is at the end of the dialyzate space facing away from the dividing wall 10, into the dialyzate space and flows through the dialyzate space in a direction opposite to that of the blood flow in the direction of dividing wall 10. In this process, it takes up the ultrafiltrate with the substances removed from the blood that are normally eliminated with the urine and is then withdrawn from the dialyzate space 12 via the outlet arrangement 14 located in the vicinity of the dividing wall 10. As also shown in FIG. 1, the substituate is withdrawn as a partial stream from the dialyzate flowing through the dialyzate supply line 19 via a substituate supply line 21 branching off from the dialyzate supply line 19, introduced into the substituate space 11 via the inlet arrangement 15, and from there delivered to the blood via the hollow-fiber membranes 3. In the embodiment depicted in FIG. 2, however, a pressure-boosting pump 23 is inserted in the substituate supply line 21 to adjust the ratio of the dialyzate volume stream to the substituate volume stream.

Figure 3:
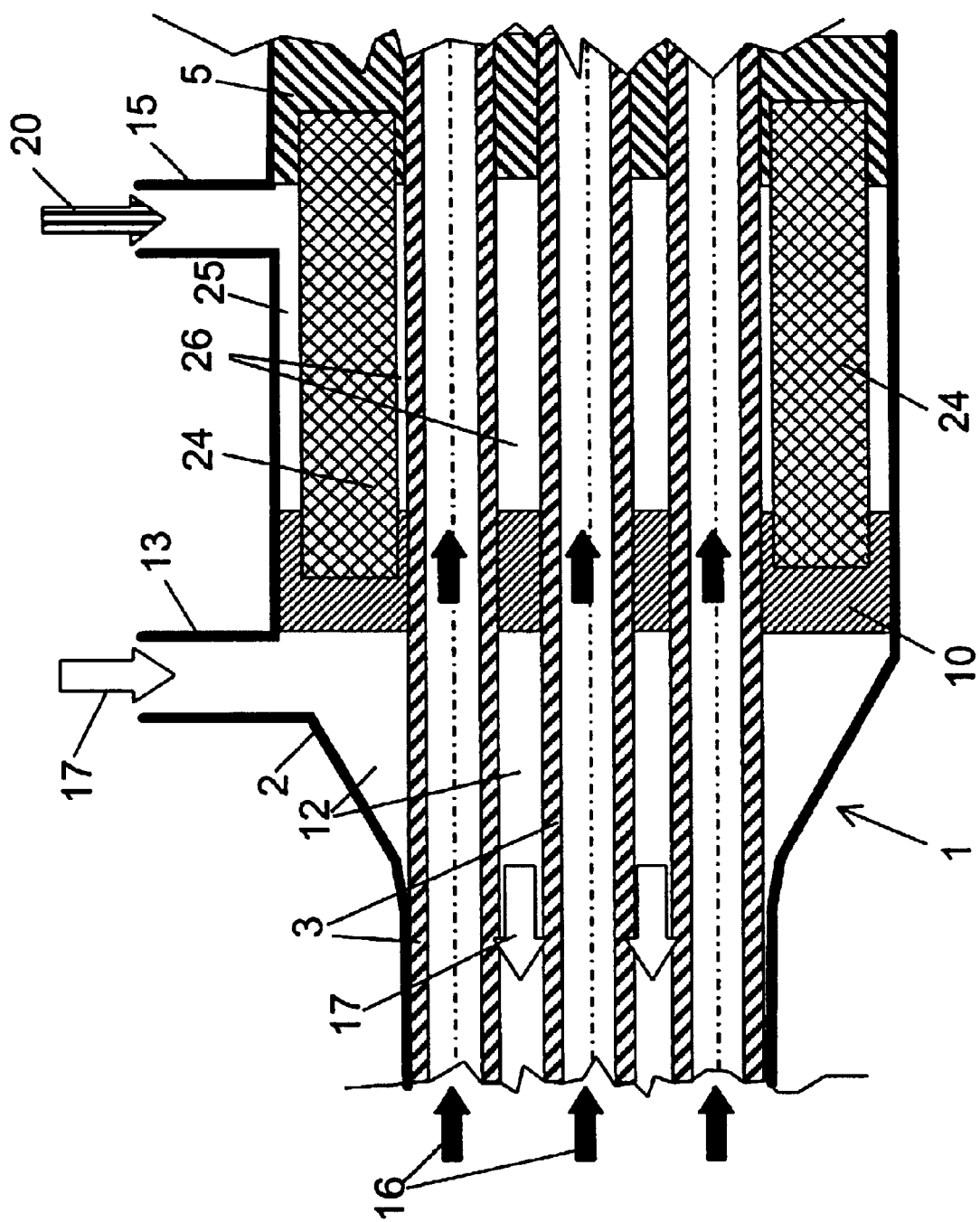
FIG. 3 represents a segment of a longitudinal section through a membrane module of the invention, or used in the hemodiafiltration system according to the invention, with a sterile filter integrated into the module housing.

FIG. 3 shows, in an enlarged representation compared to that of FIGS. 1 and 2, a segment of a membrane module 1 of the invention, or used in a hemodiafiltration system according to the invention, comprising the substituate space and the dividing wall 10. The membrane module segment depicted in FIG. 3 also corresponds substantially to that in FIG. 1, so that the same components are designated with the same reference numbers and a detailed description is not repeated.

The membrane module embodiment depicted in FIG. 3 has a sterile filter 24 integrated into housing 2 for sterile filtration of the substituate 20. The sterile filter 24, preferably in the form of a flat membrane impermeable to bacteria and endotoxins, encloses the hollow-fiber membrane bundle in the substituate space area and divides the substituate space into an outer substituate-space section 25 and an inner substituate-space section 26, each of which is separated in a fluid-tight manner from dialyzate space 12 via dividing wall 10. The sterile filter and hollow-fiber membranes 3 can readily be embedded in the sealing compound 5 and dividing wall 10. During use of the embodiment of the membrane module according to the invention, as shown in FIG. 3, the substituate 20 introduced into the housing via the inlet arrangement 15 is distributed uniformly in the outer substituate-space section 25 over the entire periphery and flows completely through the sterile filer 24, where it is subjected to sterile filtration. After flowing through the sterile filter 24, the substituate 20 is distributed over the inner substituate-space section 26 and flows from there through the walls of the hollow-fiber membranes 3 into the blood flowing through them.

Figure 4:
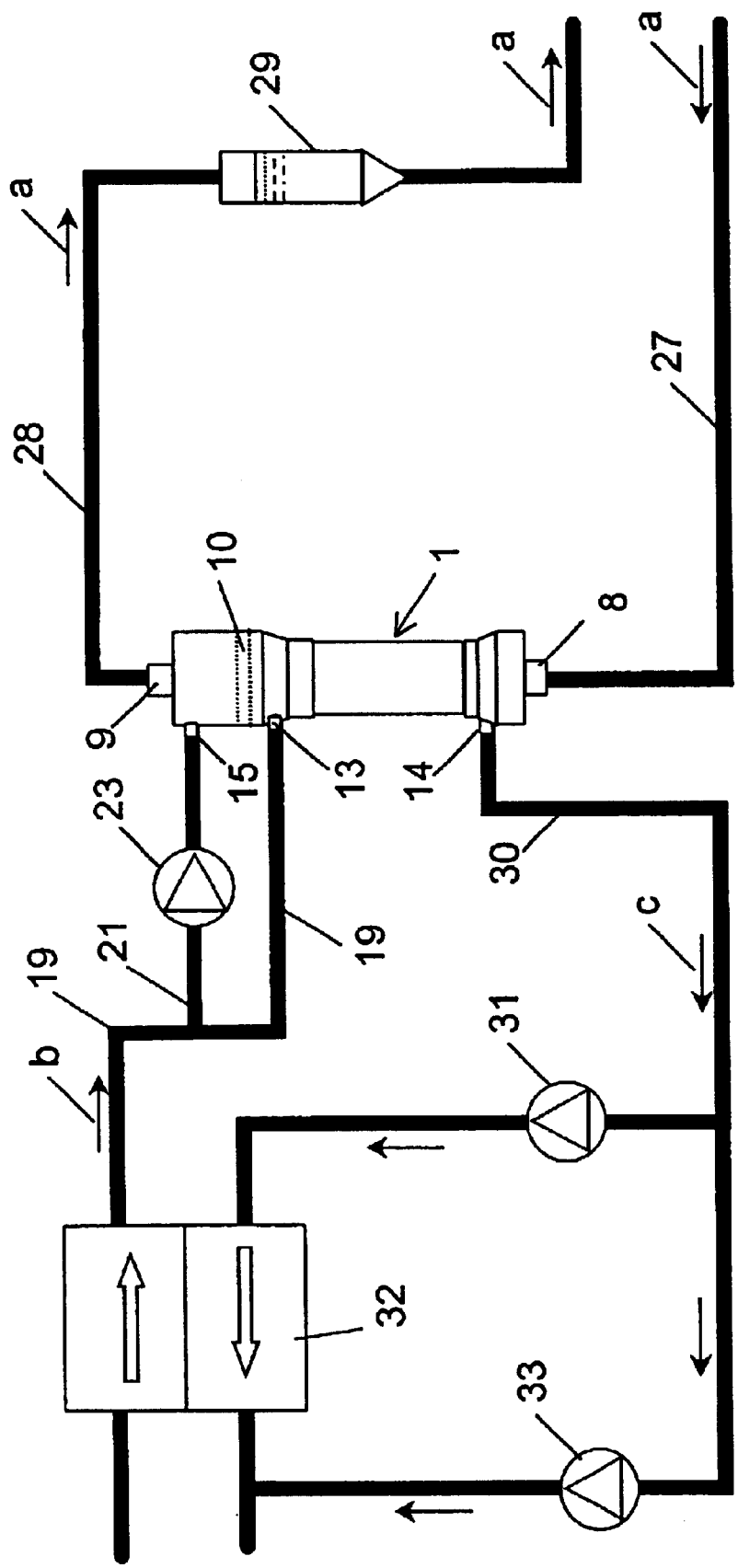
FIG. 4 is a schematic representation of a hemodiafiltration system of the invention, illustrating a process with post-dilution of blood.

FIG. 4 is a schematic representation of the basic construction of a hemodiafiltration system of the invention, comprising a membrane module 1 with a dividing wall 10, as is shown in FIG. 1. The hemodiafiltration system of FIG. 4 is suitable for hemodiafiltration processes in which a post-dilution of the blood with substituate is performed. The blood taken from the patient is delivered to membrane module 1 in the direction of arrow "a" via a blood supply line 27 and the blood inlet arrangement 8 of the membrane module 1 serving as a hemodiafilter and passed through the lumina of the hollow-fiber membranes arranged in the membrane module. The purified blood is withdrawn from membrane module 1 via the blood outlet arrangement 9 and re-introduced to the patient in the direction of arrow "a" via blood withdrawal line 28 and drip chamber 29.

Dialyzate is delivered in the direction of arrow "b" via the dialyzate supply line 19 and dialyzate inlet arrangement 13 into the dialyzate space of the hemodiafilter 1, flowing through the dialyzate space toward the dialyzate outlet arrangement 14 in a direction opposite to that of the blood flow, thereby taking up the ultrafiltrate, containing the substances normally eliminated with the urine, that is withdrawn from the blood via the hollow-fiber membranes. The dialyzate, enriched with the ultrafiltrate, leaves the membrane module via the outlet arrangement 14 and is conducted away via the dialyzate withdrawal line 30 in the direction of arrow "c" using dialyzate flow pump 31 and ultrafiltrate pump 33.

In the embodiment of the hemodiafiltration system of the invention as depicted in FIG. 4, the substituate to be delivered to the blood is introduced through the substituate supply line 21 branching off from the dialyzate supply line 19 and via the substituate inlet arrangement 15 into the substituate space of membrane module 1, from which it is delivered to the blood flowing in the hollow-fiber membranes via their walls. In the present case, a pump 23 is located in the substituate supply line 21, which is preferably controllable and via which the substituate volume stream, and thus the ratio of dialyzate volume stream to substituate volume stream, can be adjusted.

The balancing unit 32 provides for controlling the circulation of the dialyzate, and the ultrafiltrate pump 33 for adjusting the net filtrate stream withdrawn from the blood in the area of the dialyzate space. In this process, the balancing unit 32 functions such that the volume stream delivered via pump 31 is replaced by an identically large volume stream of fresh dialyzate.

Figure 5:
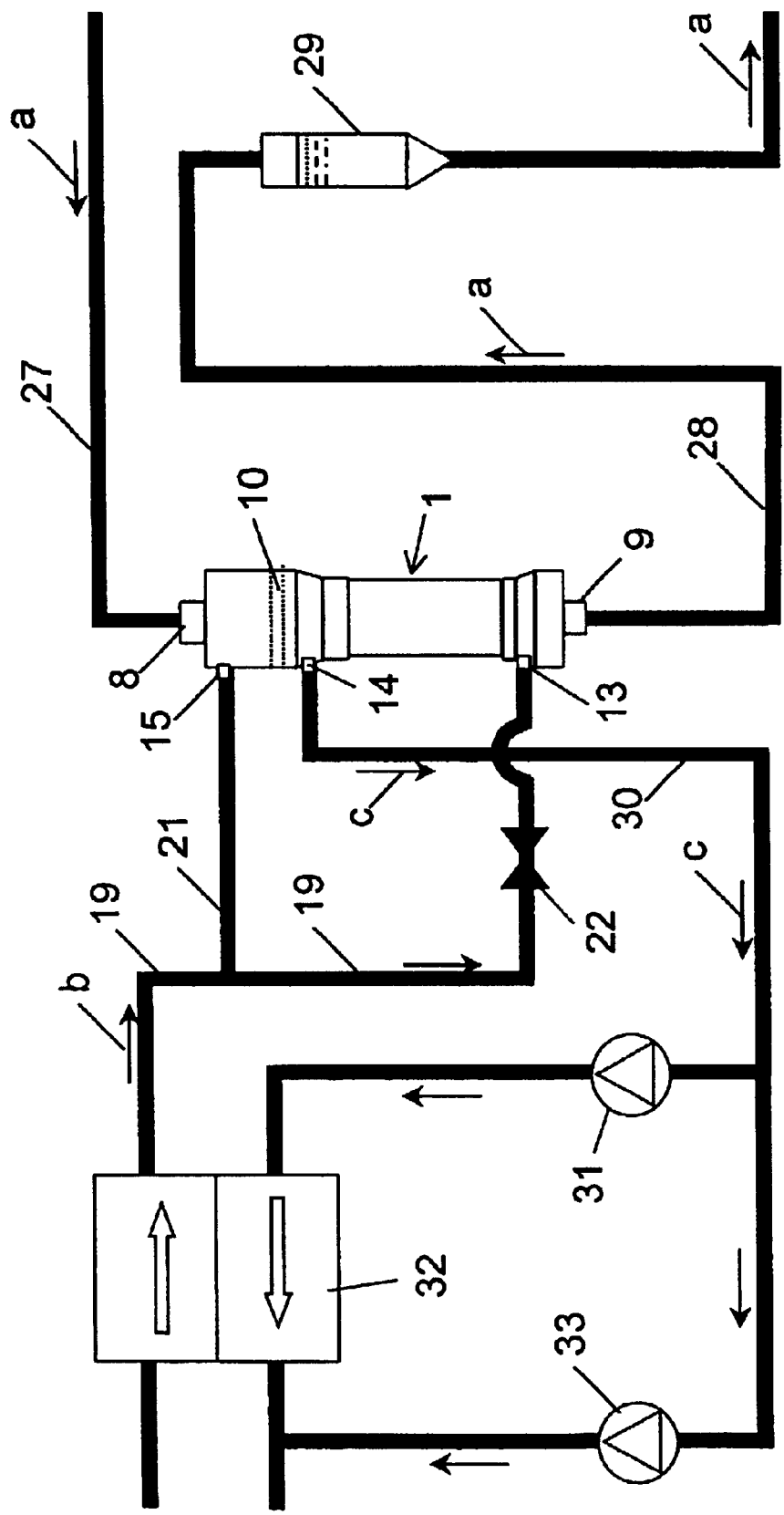
FIG. 5 is a schematic representation of a hemodiafiltration system of the invention, illustrating a process with pre-dilution of blood.

FIG. 5 schematically depicts another embodiment of the hemodiafiltration system of the invention. The major components of the hemodiafiltration system of FIG. 5 correspond to those of FIG. 4, so that the same components are designated with the same reference numbers. In contrast to the hemodiafiltration system of FIG. 4, however, the hemodiafiltration system of FIG. 5 is suited to hemodiafiltration processes in which a pre-dilution of the blood with substituate is performed. The dialyzate, which is delivered via the dialyzate supply line 19 to membrane module 1 serving as a hemodiafilter, flows via the dialyzate inlet arrangement 13 into the dialyzate space of the hemodiafilter, the dialyzate inlet arrangement 13 being located in the present case at the end of the hemodiafilter facing toward the blood outlet arrangement 9. In the dialyzate space, the dialyzate flows, in a direction opposite that of the blood, toward the dialyzate outlet arrangement 14, which is arranged adjacent to the dividing wall 10, which is merely suggested in this case. The dialyzate, mixed with the ultrafiltrate taken up in the dialyzate space, leaves the dialyzate space via the dialyzate outlet arrangement 14 and is withdrawn via the dialyzate withdrawal line 30 in the direction of arrow "c" using dialyzate flow pump 31 and ultrafiltrate pump 33.

In the embodiment of the hemodiafiltration system of the invention as shown in FIG. 5, the substituate to be delivered to the blood is likewise diverted from the dialyzate stream through a substituate supply line 21 branching off from the dialyzate supply line 19 and introduced via the substituate inlet arrangement 15 into the substituate space of membrane module 1, from which it is delivered to the blood flowing in the hollow-fiber membranes via their walls. In the embodiment of the hemodiafiltration system of the invention as shown in FIG. 5, a throttle 22 is present in the dialyzate supply line 19 between the diversion of the substituate supply line 21 and the dialyzate inlet arrangement 13, the throttle being preferably in the form of an adjustable valve by which the ratio of dialyzate volume stream to substituate volume stream is adjusted.

What is claimed is:

1. A hemodiafiltration system for treating blood, comprising a membrane module having a cylinder-shaped housing with a longitudinal extent, in which housing hollow-fiber membranes having semipermeable walls and being capable of supporting fluid flow through their lumina are arranged in a direction of the longitudinal extent of the housing, one end of the hollow-fiber membranes being embedded in a fluid-tight manner in a first sealing compound joined to an inner wall of the housing in a fluid-tight manner and a second end of the hollow-fiber membranes being embedded in a fluid-tight manner in a second sealing compound joined to the inner wall of the housing in a fluid-tight manner, and comprising a dialyzate space into which a dialyzate inlet arrangement and a dialyzate outlet arrangement open, a substituate space into which a substituate inlet arrangement opens, and a means for delivering a dialyzate having a defined volume stream into the dialyzate space via the dialyzate inlet arrangement, a means for withdrawing the dialyzate from the dialyzate space via the dialyzate outlet arrangement, and a means for delivering a substituate with a defined volume stream into the substituate space via the substituate inlet arrangement, wherein the membrane module is implemented as an integrated unit for blood treatment, filtration of the substituate, and mixing of the substituate with the blood, and the substituate space and dialyzate space are separated from each other in a manner via a continuous dividing wall, wherein the hollow-fiber membranes are combined into a single bundle and are used for blood treatment, filtration of the substituate, and delivery of the substituate to the blood, such that an exterior space delimited by the inner wall of the housing and the first and second sealing compounds are formed around the hollow-fiber membranes, wherein the exterior space along the longitudinal extent of the housing is separated by the dividing wall into the substituate space and the dialyzate space, and the dividing wall encloses each individual hollow-fiber membrane.

2. The hemodiafiltration system according to claim 1, wherein the dividing wall is arranged substantially transversely to the hollow-fiber membranes.

3. The hemodiafiltration system according to claim 1, wherein the means for delivering the substituate and the means for delivering dialyzate are coupled to each other.

4. The hemodiafiltration system according to claim 3, wherein the means for delivering substituate and the means for delivering dialyzate comprise a common multiple pump to which a dialyzate supply line in communication with the dialyzate inlet arrangement and a substituate supply line in communication with the substituate inlet arrangement are connected.

5. The hemodiafiltration system according to claim 3, wherein the means for delivering dialyzate comprises a dialyzate delivery device and a dialyzate supply line, and the means for delivering substituate comprises a substituate supply line, wherein the substituate supply line branches off from the dialyzate supply line via a diversion.

6. The hemodiafiltration system according to claim 5, wherein a substituate pump is inserted in the substituate supply line for delivering the substituate.

7. The hemodiafiltration system according to claim 5, wherein a throttle is inserted in the dialyzate supply line in an area between the diversion and the dialyzate inlet arrangement or into the substituate supply line and the dialyzate supply line in the area between the diversion and the dialyzate inlet arrangement, in order to adjust a ratio of substituate volume stream to dialyzate volume stream.

8. The hemodiafiltration system according to claim 1, wherein the membrane module in an area of substituate space has a sterile filter arranged around the bundle of hollow-fiber membranes and enclosing the bundle.

9. The hemodiafiltration system according to claim 8, wherein the sterile filter is a microporous flat membrane.

10. The hemodiafiltration system according to claim 1, wherein the membrane module, viewed in a direction of the longitudinal extent of the housing, exhibits a ratio $L_d/L_s$ of a length $L_d$ of the dialyzate space to a length $L_s$ of the substituate space between 3 and 20.

11. The hemodiafiltration system according to claim 10, wherein the ratio $L_d/L_s$ is between 5 and 15.

12. The hemodiafiltration system according to claim 1, wherein the dividing wall of the membrane module comprises a cured sealing compound.

13. The hemodiafiltration system according to claim 12, wherein the dividing wall and the first and second sealing compounds comprise the same material.

14. The hemodiafiltration system according to claim 1, wherein the dividing wall of the membrane module has a thickness between 1 and 15 nun.

15. The hemodiafiltration system according to claim 1, wherein an inside of the housing of the membrane module tightly encloses the bundle of hollow-fiber membranes in an area of the dialyzate space and exhibits an expanded cross-section in an area of the sealing compounds, dividing wall, and substituate space.

16. The hemodiafiltration system according to claim 1, wherein the hollow-fiber membranes of the membrane module have an ultrafiltration rate for water between 20 and 1500 ml/(h·m²·mmHg).

17. The hemodiafiltration system according to claim 1, wherein the hollow-fiber membranes of the membrane module are impermeable to endotoxins.

18. A hemodiafiltration process comprising:

Introducing blood into a blood inlet at one end of a membrane module having a cylinder-shaped housing with a longitudinal extent, in which housing a bundle of hollow-fiber membranes having semipermeable walls and being capable of supporting fluid flow through their lumina is arranged in a direction of the longitudinal extent of the housing, one end of the hollow-fiber membranes being embedded in a fluid-tight manner in a first sealing compound joined to an inner wall of the housing in a fluid-tight manner and a second end of the hollow-fiber membranes being embedded in a fluid-tight manner in a second sealing compound joined to the inner wall of the housing in a fluid-tight manner, and in which housing an exterior space delimited by the inner wall of the housing and the first and second sealing compounds are formed around the hollow-fiber membranes, wherein the exterior space along the longitudinal extent of the housing is divided by a continuous dividing wall into a dialyzate space and a substituate space separated from the dialyzate space in a fluid-tight manner, and the dividing wall encloses each individual hollow-fiber membrane, directing the blood through the lumina of the hollow-fiber membranes, introducing a dialyzate into the dialyzate space, passing the dialyzate along the hollow-fiber membranes, thereby taking up an ultrafiltrate withdrawn from the blood through the walls of the hollow-fiber membranes, withdrawing the dialyzate mixed with the ultrafiltrate from the dialyzate space, introducing a substituate into the substituate space, delivering the substituate to the blood via the walls of the hollow-fiber membranes, and withdrawing the blood from a blood outlet at the other end of the membrane module.

19. A membrane module comprising a cylinder-shaped housing with a longitudinal extent, in which housing a bundle of hollow-fiber membranes having semipermeable walls and being capable of supporting fluid flow through lumina is oriented in a direction of the longitudinal extent of the housing, one end of the hollow-fiber membranes being embedded in a fluid-tight manner in a first sealing compound joined to an inner wall of the housing in a fluid-tight manner and a second end of the hollow-fiber-membranes being embedded in a fluid-tight manner in a second sealing compound joined to the inner wall of the housing in a fluid-tight manner, such that an exterior space delimited by the first and second sealing compounds and the inner wall of the housing is formed around the hollow-fiber membranes, wherein the exterior space along the longitudinal extent of the housing is divided into a dialyzate space and a substituate space by a dividing wall that encloses each hollow-fiber membrane and runs substantially transversely to the hollow-fiber membranes, wherein the dialyzate space has an inlet arrangement and an outlet arrangement for introducing and withdrawing a dialyzate, and the substituate space has at least one inlet arrangement for introducing a substituate, wherein a sterile filter is arranged in an area of the substituate space between the substituate inlet arrangement and the hollow-fiber membranes located in the substituate space, such that the sterile filter divides the substituate space into an outer substituate-space section and an inner substituate-space section that is spatially separated from the outer substituate-space section, and wherein the outer substituate-space section is in fluid communication with the substituate inlet arrangement and the hollow-fiber membranes are arranged in the inner substituate-space section.

20. The membrane module according to claim 19, wherein the sterile filter is arranged around the bundle of hollow-fiber membranes and encloses the bundle of hollow-fiber membranes.

21. The membrane module according to claim 19, wherein the sterile filter is a microporous flat membrane.

22. The membrane module according to claim 19, wherein the sterile filter is impermeable to endotoxins.

* * * * *

UNITED STATES PATENT AND TRADEMARK OFFICE
CERTIFICATE OF CORRECTION

PATENT NO. : 6,776,912 B2
DATED : August 17, 2004
INVENTOR(S) : Ulrich Baurmeister It is certified that error appears in the above-identified patent and that said Letters Patent is hereby corrected as shown below:

Column 2,
Line 53, change "Modem" to -- Modern --.

Column 11,
Line 61, change "pm" to -- $\mu$m --.

Column 17,
Line 22, change "nun" to -- mm --.
Line 37, change "Introducing" to -- introducing --.

Signed and Sealed this

Thirtieth Day of November, 2004

JON W. DUDAS
*Director of the United States Patent and Trademark Office*